United States Patent [19]
Baiocchi

[11] Patent Number: 5,739,334
[45] Date of Patent: Apr. 14, 1998

[54] ALKYL DERIVATIVES OF TRAZODONE WITH CNS ACTIVITY

[75] Inventor: Leandro Baiocchi, Rome, Italy

[73] Assignee: Istituto Ricerca Francesco Angelini S.p.A., Pomezia, Italy

[21] Appl. No.: 457,114

[22] Filed: Jun. 1, 1995

Related U.S. Application Data

[62] Division of Ser. No. 256,352, Jul. 18, 1994, abandoned.

[30] Foreign Application Priority Data

Jan. 17, 1992 [IT] Italy .................................. MI92A0084

[51] Int. Cl.⁶ .................... C07D 241/08; C07D 241/04
[52] U.S. Cl. .................... 544/384; 544/392; 544/394; 544/395
[58] Field of Search .................... 544/392, 394, 544/395, 384

[56] References Cited

U.S. PATENT DOCUMENTS

| T100,505 | 4/1981 | Morrow et al. | 544/366 |
|---|---|---|---|
| 3,365,453 | 1/1968 | Archer | 544/384 |
| 3,381,009 | 4/1968 | Palazzo et al. | 544/362 |
| 4,073,908 | 2/1978 | Quelet | 544/395 |

OTHER PUBLICATIONS

Morrow et al Defensive Publication, Application Serial No. 06/130,900 filed Mar. 17, 1980, laid open to public inspection on Mar. 7, 1981.

Fuller et al, *Chemical Abstracts*, vol. 93, No. 61019 (1980).

*Primary Examiner*—Emily Bernhardt
*Attorney, Agent, or Firm*—Oblon, Spivak, McClelland, Maier & Neustadt, P.C.

[57] ABSTRACT

Alkyl derivatives of trazodone endowed with pharmacological activity, pharmaceutical compositions containing them, process for preparing them and intermediate compounds useful in their preparation are disclosed.

2 Claims, No Drawings

ALKYL DERIVATIVES OF TRAZODONE WITH CNS ACTIVITY

This is a Division, of application Ser. No. 08/256,352 filed on Jul. 18, 1994, now abandoned which was filed as International Application No. PCT/EP93/00080 filed Jan. 14, 1993.

DESCRIPTION

The present invention relates to novel alkyl derivatives of trazodone endowed with pharmacological activity, pharmaceutical compositions containing them, a process for preparing them and intermediate compounds useful in their preparation.

Now, it has been surprisingly found that the compounds of the formula (I)

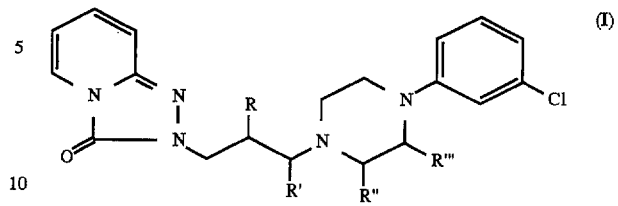

wherein only one of R, R', R" and R'" is 1–3 C alkyl and the others are H,
and the acid addition salts thereof with physiologically acceptable organic or inorganic acids,
have a reduced affinity for adrenergic receptors (see the following table):

|  | alpha 1 (% inhibition) | | serotonine 2 (% inhibition) | |
|---|---|---|---|---|
|  | $C = 10^{-7}$ M | $C = 10^{-5}$ M | $C = 10^{-7}$ M | $C = 10^{-5}$ M |
| (I) R = R' = R" = R'" = H (trazodone) | 49 | 98 | 78 | 103 |
| (I) R = R' = R'" = H; R" = CH$_3$ | 37 | 96 | 69 | 100 |
| (I) R = R' = R" = H; R'" = CH$_3$ | 20 | 85 | 68 | 98 |
| (I) R = R" = R'" = H; R' = CH$_3$ | 26 | 91 | 59 | 100 |
| (I) R' = R" = R'" = H; R = CH$_3$ | 27 | 88 | 62 | 100 |

Trazodone of formula (T) is a drug which has been known for over twenty years and has been widely used as an antidepressant (T)

On the other hand, some Authors also reported some diazepine-like clinical actions for this drug (Burger's Medicinal Chemistry, 4th ed. (1981)).

Although it has still to be completely understood, it is almost certain that its mechanism of action is related to the interference of trazodone with the system of aminergic transmission of the central nervous system.

Chemical bond studies have shown that trazodone exhibits a certain degree of interference with the following receptors:

|  | (% inhibition) | |
|---|---|---|
|  | $C = 10^{-5}$ M | $C = 10^{-7}$ M |
| alpha 1 | 98.2 | 49.0 |
| alpha 2 | 75.1 | less than 45.0 |
| sigma | 81.7 | less than 45.0 |
| serotonin 1 | 79.8 | less than 45.0 |
| serotonin 2 | 102.8 | 78.3 |
| histamine 1 | 83.1 | less than 45.0 |
| serotonin reuptake | 96.0 | less than 45.0 |

The action on the adrenergic receptors (alpha 1 and alpha 2) seems to be responsible for some sporadic side effects of trazodone, such as hypotension and priapism, while it does not have a part, as far as our present knowledge is concerned, in the psychopharmacological activities.

Furthermore, the compounds of the formula (I) are superior to trazodone even as far as the DL$_{50}$ is concerned

|  | DL$_{50}$ |
|---|---|
| (I) R = R' = R" = R'" = H (trazodone) | $\geq$ 200 |
| (I) R = R' = R'" = H; R" = CH$_3$ | 300 |
| (I) R = R' = R" = H; R'" = CH$_3$ | $\leq$ 600 |
| (I) R = R" = R'" = H; R' = CH$_3$ | $\leq$ 300 |
| (I) R' = R" = R'" = H; R = CH$_3$ | $\leq$ 600 |

Therefore, it is a first object of the present invention to provide a compound of the formula (I) wherein only one of R, R', R" and R'" is 1–3 C alkyl and the others are H, and the acid addition salts thereof with physiologically acceptable organic or inorganic acids.

Examples of suitable physiologically acceptable inorganic and organic acids are hydrochloric, hydrobromic, phosphoric, sulphuric, lactic, succinic, tartaric, acetic, citric, benzoic, naphthalene-2-sulfonic, adipic, and pimelic acid.

Preferably, the compounds of the formula (I) are prepared according to the following reaction scheme reaction scheme 1

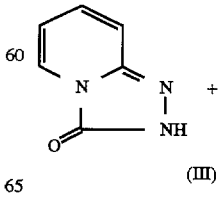

(III)

-continued
reaction scheme 1

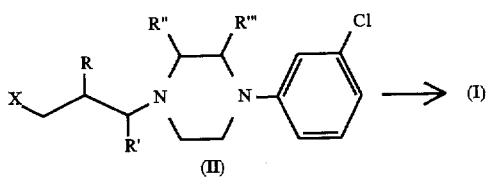

where R, R', R" and R'" are as described above, and

X is a conventional leaving group selected from the class comprising chlorine, bromine, —O—SO$_2$Alk, and —O—SO$_2$Ar.

The step shown in the reaction scheme 1 substantially involves the alkylation of an aliphatic secondary amino group and can be performed according to conventional techniques (J. March, Advanced Organic Chemistry, 3rd Ed., J. Wiley & Sons, N.Y., pages 364–365).

The compound of the formula (III) is preferably reacted in the form of a salt thereof with an alkali metal such as, for example, the sodium salt described in the U.S. Pat. No. 3,381,009.

In the leaving groups —O—SO$_2$Alk and —O—SO$_2$Ar, Alk and Ar mean alkyl and aryl (J. March, Advanced Organic Chemistry, 3rd Ed., J. Wiley & Sons, N.Y., page 312). Preferably, Alk is methyl and Ar is phenyl, tolyl, and p-bromo-phenyl.

The reaction is preferably carried out by reacting the sodium salt of the compound of the formula (III) with a compound of the formula (II) in the presence of a suitable organic diluent or a mixture of organic diluent at a temperatura of from 40° C. and the boiling temperature of the reaction mixture. Examples of suitable organic diluents are the aromatic hydrocarbons, the aliphatic alcohols, and mixtures thereof.

Examples of preferred aromatic hydrocarbons are: benzene, toluene and xylene. Examples of preferred aliphatic alcohols are butyl, t-butyl, s-butyl, isobutyl, pentyl, and t-pentyl alcohol. An example of a preferred amide is dimethylformamide.

The intermediate compound of the formula (II) is novel.

Therefore, it is a further object of this invention to provide a compound of the formula (II) wherein R, R', R", R'" and X are as described above.

The intermediate compounds of the formula (II) may be prepared according to the following reaction scheme reaction scheme 2

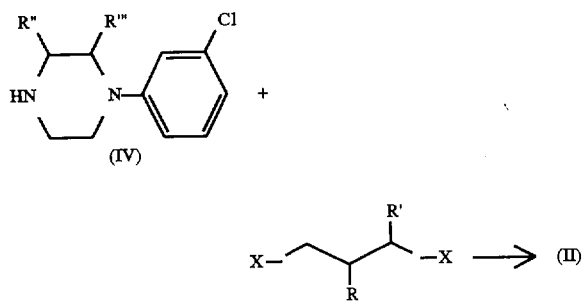

where X, R, R', R" and R'" are as described above.

The step shown in the reaction scheme 2 is preferably performed by adding a piperazine compound of the formula (IV) to an aqueous mixture of a difunctional alkylating agent of the formula X—CH$_2$—CHR—CHR'—X with a suitable alkali metal derivative.

The piperazine compound of the formula (IV) is preferably dissolved into a suitable organic diluent such as, for example, an aromatic hydrocarbon or a keton. Examples of suitable aromatic hydrocarbons are benzene, toluene and xylene. Examples of suitable ketons are acetone and methyl isobutyl keton.

Examples of suitable alkali metal derivatives are sodium and potassium carbonate or hydroxide.

The piperazine compound of the formula (IV) wherein R"=R'"=H is known (G. B. Pollard et al., J.O.C. 24, 764 (1959)) while the compounds of formula (IV) wherein R'" is H and R" is 1–3 C alkyl are novel and can be prepared according to the following reaction scheme reaction scheme 3

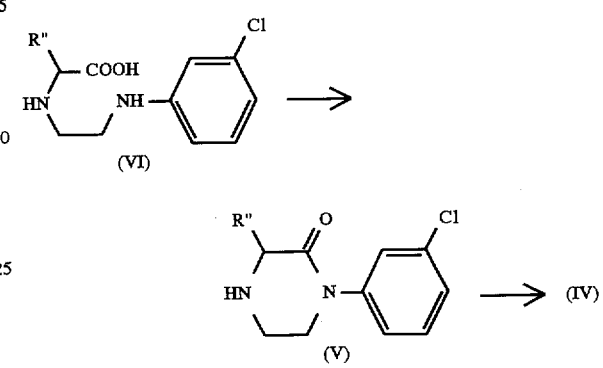

The ring closure from a 2-R"-(3-chlorophenyl)-3,6-diazahexanoic acid of the formula (VI) to yield the corresponding piperazinone of the formula (V) is preferably performed by treating a lower ester of the henoic acid of the formula (VI) with a suitable condensing agent in the presence of a diluent.

Examples of suitable condensing agents are sodium hydride, thionyl chloride and hydrogen chloride.

The diluent is selected depending on the condensing agent according to criteria well known to the person skilled in the art. For example, when the condensing agent is NaH, suitable diluents are the aromatic hydrocarbon such as benzene, toluene and xylene, while lower halogenated hydrocarbons such as chloroform and methylene chloride are preferred when thionyl chloride is the condensing agent.

The subsequent reduction of the piperazinone compounds of the formula (V) to yield the corresponding piperazine compounds of the formula (IV) is carried out with conventional reducing agent such as lithium aluminium hydride.

Both the piperazone compounds of the formula (V) and the 2-substituted (3-chlorophenyl)-3,6-diazahexanoic acids of the formula (VI) wherein R" is 1–3 C alkyl are also novel. They are therefore a further object of this invention.

The compounds of the formula (I) may have an assymetric carbon atom. It is, therefore, a further object of this invention to provide both the single optically active isomers of the formula (I) and the mixtures thereof.

The compounds of formula (I) of this invention will be useful in all those therapeutical fields where trazodone proved to be effective such as, for example, depression, without showing, however, the undesired side-effects of trazodone such as hypotension and priapism. More particularly, the compounds of formula (I) of this invention are very promising in the treatment of the anxiety state.

For practical applications in therapy the compounds of the formula (I) and their physiologically acceptable acid addition salts can be administered as they are, but it is preferred to administer them in the form of pharmaceutical compositions.

Said compositions are another object of the present invention and contain a therapeutically effective amount of one or more compounds of the formula (I) or their salts with physiologically acceptable acids together with liquid or solid pharmaceutical excipients suitable for systemic or topical administration.

The pharmaceutical compositions of the present invention can be solid, such as tablets, sugar-coated pills, capsules, powders and slow release forms, or semi-solid such as suppositories, creams and ointments, or in liquid form such as solutions, suspensions and emulsions.

In addition to the conventional excipients, the compositions may contain suitable pharmaceutical additives such as preservatives, stabilizers, emulsifiers, salts to regulate osmotic pressure, buffers, flavouring and colouring agents.

When requested by particular therapies, the compositions of this invention may comprise other compatible active ingredients whose concomitant administration is therapeutically useful.

For practical uses in therapy the effective amount of the compound of the formula (I) to be administered may vary over a rather broad range depending on known factors such as the specific therapy required, the pharmaceutical composition, the adminstration route, the body weight, and the effectiveness of the specific compound of this invention which is used. However, the optimum effective amount can readily be accomplished by simple routine procedures.

In general the daily dosage of the compounds of the formula (I) will preferably range from 10 to 600 mg; however, due to the lack of side-effects it may be increased up to 1200 mg.

The pharmaceutical compositions of this invention can be made following conventional techniques of the pharmaceutical chemist involving mixing, granulating and compressing when necessary, or variously mixing and dissolving the ingredients when appropriate to give the desired end product.

For the purpose of better illustrating the invention the following examples are now given.

EXAMPLE 1

1-(3-chlorophenyl)-3-methyl piperazin-2-one (formula (V), R"=CH$_3$)

A solution of 76 g of N-(3-chlorophenyl)-ethyldiamine (J. Med. Chem. 9, pp. 858–60 (1966)), 60 ml of ethyl 2-bromopropionate and 63 ml of triethylamine, in 400 ml of toluene, was boiled and refluxed for 15 hours.

After cooling, the solution was washed with water, dried by azeotropic distillation and 9 g of sodium hydride (oily suspension at 60%) were added gradually. Spontaneous heating of the mixture was observed during the addition of sodium hydride.

The reaction mixture was maintained under stirring at 60° C. (external heating) for 1.5 hours and then cooled. After having added water, the organic phase was separated, dried, and then evaporated under reduced pressure. The residue (48 g) was distilled to yield 35 g of 1-(3-chlorophenyl)-3-methyl-piperazin-2-one (b.p. 160° C. at 0.5 mmHg).

Its hydrochloride salt melts at 170.5°–171° C.

EXAMPLE 2

1-(3-chlorophenyl)-3-ethyl piperazin-2-one (formula (V), R"=C$_2$H$_5$)

A solution of 102 g of N-(3-chlorophenyl)-ethyldiamine, 117 g of ethyl 2-bromo butyrate and 84 ml of triethylamine, in 500 ml of toluene, was boiled and refluxed for 6 hours. The solution was cooled, washed with water and the solvent was removed under reduced pressure.

The oily residue (175 g) was suspended in 650 ml of a solution of 2M NaOH and the mixture was heated at 70° C. under vigorous stirring until dissolution of the oil was complete (after about 2 hours). The resulting solution was acidified and the solid precipitate was collected by filtration. (3-chlorophenyl)-2-ethyl-3,6-diazahexanoic acid (formula (VI), R"=ethyl) was thus obtained; m.p. 207°–208°C. The elemental analysis was in agreement with the formula $C_{12}H_{17}ClN_2O_2$.

To a solution of the above mentioned acid, in 1.8 l of chloroform, 76.1 g of thionyl chloride were added dropwise. After having boiled the resulting mixture for 3 hours, the solvent was removed by evaporation and the residue was suspended in a solution of 70 ml of triethylamine in 1.8 l of toluene. After 2 hours of heating at 70° C. under stirring, the solution was cooled, filtered to remove triethylamine hydrochloride and evaporated under reduced pressure. The residue was distilled, collecting the fraction between 195° and 200° C. at 0.3 mmHg.

The hydrochloride salt of the title compound melts at 149°–152° C.

EXAMPLE 3

1-(3-chlorophenyl)-3-ethyl piperazine (formula (IV), R"=C$_2$H$_5$)

To a suspension of 31.5 g of lithium aluminium hydride, in 650 ml of ethyl ether, a solution of 66 g of the piperazinone compound of the Example 2 in 350 ml of ethyl ether was added under vigorous stirring, dropwise so that the solvent refluxed gently.

Upon completing the addition, the resulting mixture was boiled and refluxed for a further 2 hours, then the excess of hydride was decomposed with water and the organic base so obtained was separated according to conventional techniques.

The hydrochloride salt of the title compound, recrystallized from isopropyl alcohol, melts at 179°–181° C.

EXAMPLE 4

1-(3-chlorophenyl)-3-methyl piperazine (formula (IV), R"=CH$_3$)

Following the same procedure as described in Example 3, but using the piperazinone compound of the Example 1, 1-(3-chlorophenyl)-3-methyl piperazine was obtained.

Its hydrochloride salt melts at 178°–178.5° C. (from ethyl acetate).

EXAMPLE 5

1-(3-chlorophenyl)-4-(3-chloro-2-methylpropyl)-piperazine (formula (II), R=CH$_3$, R'=R"=R'"=H)

To a mixture of 150 ml of 1-bromo-3-chloro-2-methylpropane, 55 g of potassium carbonate and 4 ml of water heated to 60° C., a solution of 40 g of 3-chlorophenyl piperazine in 50 ml of toluene was added dropwise under vigorous stirring. Upon completing the addition, the reaction mixture was maintained under stirring for 48 hours. After having filtered off the solid, the volatile portion was removed by evaporation and the residue chromatographed on a silica gel column, eluting with a mixture of hexane: ethyl acetate=1:1.

25 g of a product was thus obtained and was employed for the subsequent reaction.

The hydrochloride salt of the title compound melts at 178°–179° C. (from isopropyl alcohol).

EXAMPLE 6

Following the same procedure as described in Example 3, the suitable compounds of the formula (IV) were reacted with the suitable dihalogenalkanes to yield the following compounds of the formula (II):

1-(3-chlorophenyl)-4-(3-chloro-1-methylpropyl) piperazine (R'=CH₃, R=R"=R'"=H) Dihydrochloride salt, m.p. 160°–162° C. (dec);

1-(3-chlorophenyl)-4-(3-chloropropyl)-3-methyl-piperazine (R"=CH₃, R=R'=R'"=H) Dihydrochloride salt, m.p. 174°–176° C. (dec).

EXAMPLE 7

2-[3-[4-(3-chlorophenyl)-1-piperazine]-2-methylpropyl]-1,2,4-triazole[4,3-a]-pyridin-3-(2H)-one (formula (I), (R=CH₃, R'=R"=R'"=H)

A mixture of 43 g of the product from Example 5, 23.6 g of the sodium salt of 1,2,4 triazole[4,3-a]-pyridin-3-(2H)-one (Italian patent application No. 27806/65), 300 ml of xylene and 30 ml of isobutyl alcohol was heated and refluxed for 8 hours. The reaction mixture was diluted with an equal volume of water and the residue obtained by removing the solvents from the organic phase was transformed to the corresponding hydrochloride salt with a solution of 2M hydrochloric acid. After recrystallization from water, there were obtained 35 g of a product melting at 196°–198° C.

The elemental analysis and the spectrophometric data were in agreement with the structure of the title compound.

EXAMPLE 8

Following the same procedure as described in Example 7 the following compounds of the formula (I) were prepared:

2-[3-[4-(3-chlorophenyl)-1-piperazinyl]-3-methylpropyl]-1,2,4-triazole-[4,3-a]-pyridin-3(2H)-one (R'=CH₃, R=R"=R'"=H) (from 1,2,4-triazole-[4,3-a]-pyridin-3-(2H)-one and the compound of the formula (II) where R=R"=R'"=H, R'=CH₃) Dihydrochloride hydrate, m.p. 184°–194° C.;

2-[3-[4-(3-chlorophenyl)-1-(2-ethyl)-piperazinyl]-propyl]-1,2,4-triazole[4,3-a]-pyridin-3(2H)-one (R"=ethyl, R=R'=R'"=H) from 1,2,4 triazole-(4,3-a)-pyridin-3-(2H)-one and the compound of the formula (II) where R"=ethyl, R=R'=R'"=H) Hydrochloride salt, m.p. 180°–182° C.;

2-[3-[4-(3-chlorophenyl)-1-(2-methyl)-piperazinyl]-propyl]-1,2,4-triazole-[4,3-a]-pyridin-3(2H)-one (R"=CH₃, R=R'=R'"=H) from 1,2,4 -triazole-[4,3a]-pyridin-3-(2H)-one and the compound of the formula (II) where R"=CH₃, R=R'=R'"=H) Hydrochloride salt, m.p. 189°–190° C.;

2-[3-[4-(3-chlorophenyl)-1-(3-methyl)-piperazinyl]-propyl]-1,2,4-triazole-[4,3-a]-pyridin-3(2H)-one (R'"=CH₃, R=R'=R"=H) from 1,2,4 triazole-[4,3-a]-pyridin-3-(2H)-one and the compound of the formula (II) where R'"=CH₃, R=R'=R"=H) Hydrochloride salt, m.p. 178°–180° C.

I claim:

1. A compound of the formula (II)

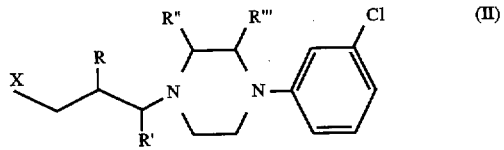

wherein

R, R' and R'" are hydrogen, and R" is methyl, and X is a conventional leaving ground selected from the class consisting of chlorine, bromine—SO₂Alkyl, and —SO₂Aryl.

2. A compound of the formula (V)

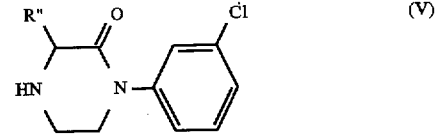

wherein R" is 1–3 C alkyl.

* * * * *